US005250502A

United States Patent [19]

Grasso

[11] Patent Number: 5,250,502

[45] Date of Patent: Oct. 5, 1993

[54] METHOD FOR ENHANCING THE HERBICIDAL ACTIVITY OF FORMULATIONS CONTAINING SOLID IMIDAZOLINYL BENZOIC ACID ESTERS WITH BISULFATE

[75] Inventor: Charles P. Grasso, Somerset, N.J.

[73] Assignee: American Cyanamid Company, Stamford, Conn.

[21] Appl. No.: 861,047

[22] Filed: Apr. 1, 1992

Related U.S. Application Data

[63] Continuation of Ser. No. 517,886, Apr. 30, 1990, abandoned.

[51] Int. Cl.[5] ........ A01N 43/50; A01N 59/02

[52] U.S. Cl. ........ 504/277; 71/DIG. 1

[58] Field of Search ........ 71/92, DIG. 1; 504/277

[56] References Cited

U.S. PATENT DOCUMENTS

| | | | |
|---|---|---|---|
| 4,188,487 | 2/1980 | Los | 548/301 |
| 4,297,128 | 2/1981 | Los | 71/92 |
| 4,334,910 | 6/1982 | Lörincz et al. | 71/82 |
| 4,554,013 | 11/1985 | Los | 71/92 |
| 4,871,388 | 10/1989 | Pasarela et al. | 71/92 |
| 4,871,392 | 10/1989 | Morgan et al. | 71/121 |

FOREIGN PATENT DOCUMENTS

| | | |
|---|---|---|
| 0256414 | 2/1988 | European Pat. Off. . |
| 2247976 | 5/1975 | France . |
| 2321845 | 3/1977 | France . |

*Primary Examiner*—Richard L. Raymond
*Assistant Examiner*—S. Mark Clardy
*Attorney, Agent, or Firm*—Peggy A. Climenson

[57] ABSTRACT

There is provided a method for enhancing the biological activity of herbicidal formulations of solid, imidazolinyl benzoic acid esters by adjusting the pH of the formulations, when diluted for spray application, to a pH of about 1.0 to 3.8 by the addition of an alkali metal bisulfate, ammonium bisulfate or a mixture thereof.

The invention also relates to a stable, non-aqueous, solid formulations of an imidazolinyl benzoic acid ester and an alkali metal bisulfate, ammonium bisulfate or a mixture thereof.

12 Claims, 1 Drawing Sheet

METHOD FOR ENHANCING THE HERBICIDAL ACTIVITY OF FORMULATIONS CONTAINING SOLID IMIDAZOLINYL BENZOIC ACID ESTERS WITH BISULFATE

This is a continuation of co-pending application Ser. No. 07/517,886, filed on Apr. 30, 1990 now abandoned.

BACKGROUND OF THE INVENTION

Imidazolinyl benzoic acids, esters and salts, methods for the preparation thereof and use of such compounds as herbicidal agents is described in U.S. Pat. Nos. 4,188,487, 4,297,128 and 4,554,013. The patented compounds are effective for the selective control of a wide variety of undesirable monocotyledonous and dicotyledonous weed species in the presence of cereal crops such as barley, wheat and rye and have been used effectively in this manner in most wheat and barley producing countries around the world. Among the most effective of these compounds is an isomeric mixture of two positional isomers, namely, 6-(4-isopropyl-4-methyl-5-oxo-2-imidazolin-2-yl)-m-toluic acid, methyl ester and 2-(4-isopropyl-4-methyl-5-oxo-2-imidazolin-2-yl)-p-toluic acid, methyl ester. In graminaceous crops such as wheat, barley and rye, this isomeric mixture has provided excellent control of many important grasses and broadleaf weeds including: wild oats (*Avena* spp.), wind grass (*Apera spicaventi*), black grass (*Alopecurus myosuroides*), wild mustard (*Brassica kaber*), wild buckwheat (*Polygonum convolvulus*), field pennycress (*Thlaspi arvense*) and wild radish (*Raphanus raphanistrum*). However, as the use of the imidazolinyl benzoic acid esters has increased and spread to grain producing countries all around the world, it has become increasingly evident that the limited solubility of the above-said esters in aqueous solutions restricts the concentrations of ester obtainable in such solutions and hence their use in aqueous sprays. Thus, it was that Paserala et al U.S. Pat. No. 4,871,388 issued Oct. 2, 1989, devised a formulation which provided a water dispersible liquid concentrate of the ester containing 0.2 to 1 molar equivalents of polybasic acid and a water miscible organic solvent. In this formulation the imidazolinyl benzoic acid ester is dissolved in the water miscible solvent and remains in solution when the concentrate is diluted with water for spray application. Although this formulation is highly effective and extensively used it is not entirely satisfactory since crystalization of the ester may occur under adverse temperature conditions and the use of organic solvent is sometimes considered objectionable.

As viewed today, organic solvents are recognized as having a potential deletarious effect upon the environment. Moreover, the use of organic solvents in the preparation of pesticide formulations can be hazardous to workmen in the formulation and packaging plants and, likewise, to the farmer who is exposed to the formulations during pesticide application if the handling of such formulations is not adequately controlled. Additionally, it is well recognized that use of organic solvents in the preparation of pesticide formulations generally increases the cost of the product, both in manufacture and shipping of the finished formulation.

It would, therefore, be most advantageous if the imidazolinyl benzoic acid esters of this invention could be formulated in a manner which would be (1) free of organic solvents, (2) readily dispersed in water for application to the foliage of plants and soil and (3) exhibit enhanced biological activity over an equivalent amount of the ester suspension concentrate formulation applied alone.

SUMMARY OF THE INVENTION

Figure 1:
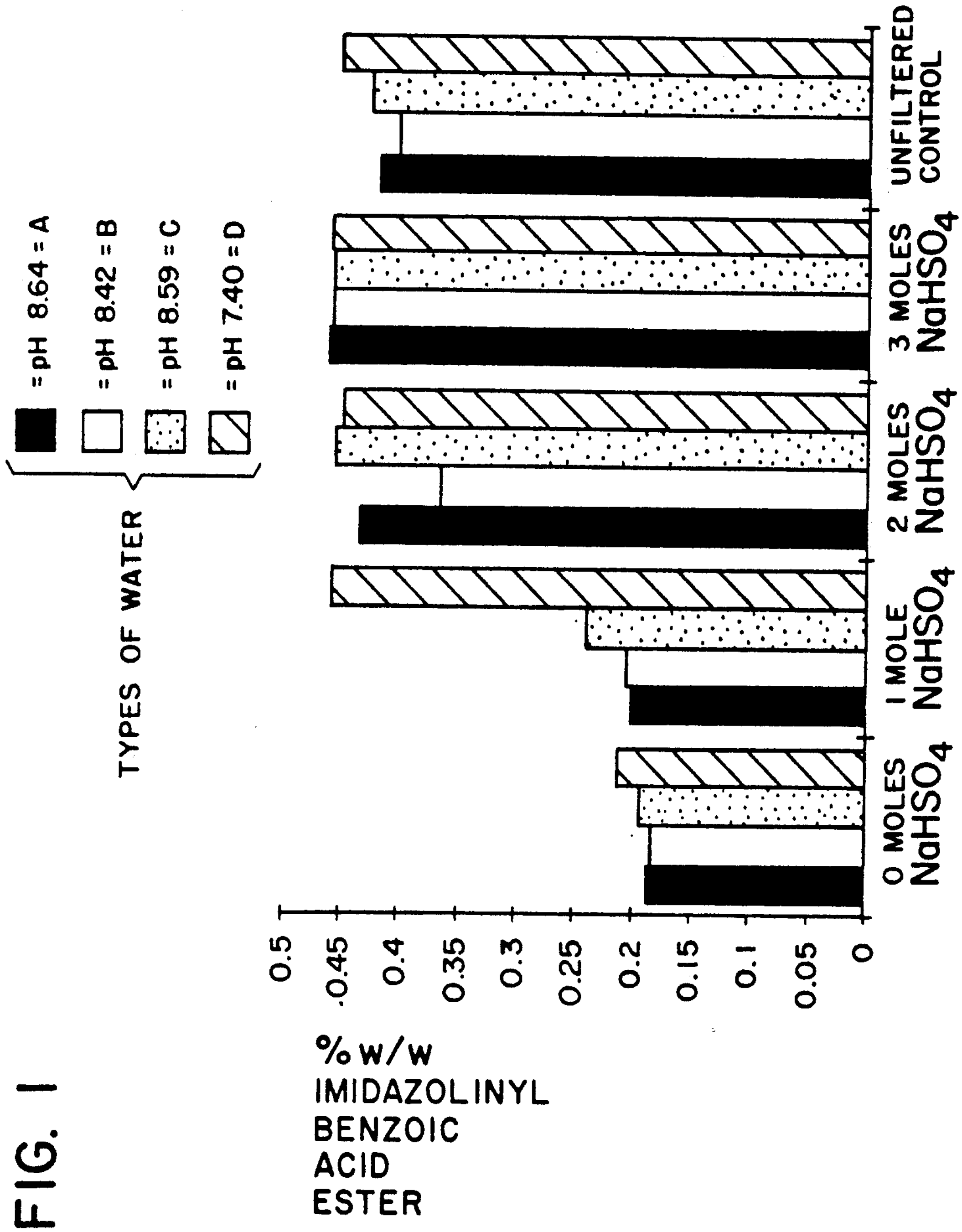
FIG. 1 shows the percent of imidazolinyl benzoic acid ester in solution versus molar equivalents of $NaHSO_4$ added, as indicated in Tables VII and VIII, below.

The present invention relates to a method for enhancing the biological activity of aqueous herbicidal dispersions, suspensions, emulsions and the like, in which the herbicidal agent is present as a finely divided, particulate, imidazolinyl benzoic acid ester, by adjusting the pH of said aqueous dispersion, suspension, emulsion or the like upon dilution for spraying, to a pH of from 1.0 to 3.8 and preferably to a value between pH 2.0 and pH 3.5, with an alkali metal bisulfate ammonium bisulfate, or mixture thereof.

More particularly, the invention relates to aqueous herbicidal compositions as described above, wherein the herbicidal agent is an isomeric mixture of finely divided, particulate, 6-(4-isopropyl-4-methyl-5-oxo-2-imidazolin-2-yl)-m-toluic acid, methyl ester and 2-(4-isopropyl-4-methyl-5-oxo-2-imidazolin-2-yl)-p-toluic acid, methyl ester and the pH of the aqueous composition, when diluted with water for application, is adjusted to a pH value between pH 1.0 and pH 3.8 and preferably between pH 2.0 and 3.5 pH by addition thereto of from 1.0 to 3.0 molar equivalents of sodium bisulfate, potassium bisulfate ammonium bisulfate or mixtures thereof per mol of ester present in said aqueous composition.

The invention also relates to stable, non-aqueous, solid compositions comprising from 10% to 55% by weight of a mixture of solid particulate 6-(4-isopropyl-4-methyl-5-oxo-2-imidazolin-2-yl)-m-toluic acid, methyl ester and 2-(4-isopropyl-4-methyl-5-oxo-2-imidazolin-2-yl)-p-toluic acid methyl ester; and from 45% to 90% by weight of sodium bisulfate, potassium bisulfate, ammonium bisulfate or mixtures thereof. Preferred solid compositions are generally comprised of 45% to 55% by weight of the isomeric mixture of the imidazolinyl toluic acid methyl esters and about 55% to 45% by weight of the alkali metal or ammonium bisulfate.

Because of the limited solubility of imidazolinyl benzoic acid esters in water and many other solvents, such esters have been formulated for agricultural application as wettable powders, water dispersible granules, aqueous suspension concentrates and the like. These formulations are generally dispersed in water for application to plants, shrubs, soil or the locus of treatment in the form of an aqueous spray containing the imidazolinyl benzoic acid ester as finely divided solid particles. These aqueous sprays are highly effective for the control of a wide variety of weed species but would be of significantly greater value to the farmer if the herbicidal activity of said sprays could be enhanced.

Surprisingly, this invention achieves the above-said desirable biological enhancement of the ester-containing sprays. Moreover, the present invention eliminates use of organic solvents in the imidazolinyl benzoic acid ester formulations, thus avoiding problems frequently associated with the manufacture, handling or application of solvent-containing formulations. The compositions prepared by the method of the present invention also have the added advantage that they permit the application of lower dosages of the imidazolinyl benzoic acid esters while achieving the desired level of weed control and do not contaminate the environment with organic solvents.

Moreover, these advantages are obtained using innocuous alkali metal or ammonium bisulfates rather than strong acids which could be difficult and hazardous to handle at the application site. Importantly, it also appears that the use of alkali metal bisulfate and/or ammonium bisulfate with the aqueous formulations containing solid, particulate imidazolinyl benzoic acid ester unexpectedly increases the uptake of the imidazolinyl compound by the plants to which it is applied.

Typical suspension concentrate formulations which can be biologically enhanced, when diluted with water for spray application and pH adjusted in accordance with the present invention, have the following compositions:

| Suspension Concentrates<br>Compound | % w/v |
|---|---|
| Imidazolinyl benzoic acid ester | 20.0-30.0 |
| Ethoxylated Nonyl phenol with 8-12 Mols of ethoxylation (Nonionic surfactant) | 12.0-20.0 |
| Oxyethoxylated polyaryl phosphate neutralized with triethanolamine (Dispersing Agent) | 1.0-4.0 |
| Butyl capped ethylene oxide/propylene oxide block copolymer (Nonionic surfactant) | 1.0-3.0 |
| Propylene glycol | 0.75-3.0 |
| Silicone antifoam | 0.50-1.0 |
| Preservative-aqueous dipropylene glycol solution of 1,2-benzisothiazolin-3-one | 0.1-0.2 |
| water q.s. to | 100.00 |

The tradenames and descriptions the ingredients employed in the preparation of the above-identified formulations are listed below along with the names of the manufacturers marketing such chemicals.

| Tradenames | Chemical Description | Manufacturer |
|---|---|---|
| Arkopal N-080 | 8 mole nonyl phenol ethoxylate | Hoechst |
| N-110 (Nonionic surfactant) | 11 mole nonyl phenol ethoxylate | Hoechst |
| Soprophor FL (Dispersing Agent) | Oxythoxylated polyarl phosphate neutralized with triethanolamine | Rhone-Poulenc |
| Silcolapse 5000 | Silicone antifoam | I.C.I. Ltd. |
| Silica FK 320 | Precipitated amorphous silica | |
| Proxel GXL (Preservative) | Aqueous dipropylene glycol solution of 1,2-Benzisothiazolin-3-one | I.C.I. Ltd. |
| Witconol NS 500K (Dispersing Agent) | Nonionic surfactant: a butyl capped ethylene oxide/propylene oxide block copolymer | WITCO S.A. |
| EMCOL 4061 | butyl capped ethylene oxide/propylene oxide block copolymer/propylene glycol ratio = 1/3/1.29 (70% in propylene glycol) | WITCO S.A. |

Typical aqueous flowable formulations that can be enhanced by the method of the present invention are described below:

| Aqueous Flowable Concentrates<br>Compound | % w/v |
|---|---|
| Imidazolinyl Benzoic Acid Ester | 20-40 |
| Polyethoxylated nonylphenols ethoxylated with 8-12 Mols of ethoxylation (Nonionic surfactant) | 12-20 |
| Polyethoxylated polyarylphenol phosphate, neutralized with triethanolamine (dispersing agent) | 3-5 |
| Silicone antifoam agent | 0.5-1.0 |
| Water q.s. to | 100.0 |

Polyoxyethylene nonylphenols suitable for use in flowable concentrate compositions of the invention

| Average Ethoxylation (moles) | Kinematic viscosity (25% aqueous solution) centistokes |
|---|---|
| 9.5 | 102 |
| 9.5 | 87 |
| 10.0 | 53 |
| 10.0 | 43 |
| 10.0 | 22 |
| 10.5 | 18 |
| 11.0 | 30 |
| 12.0 | 13 |

To prepare effective aqueous flowable concentrates, free of clays and soluble gums and containing 20% to 40% by weight of finely divided, solid, particulate imidazolinyl benzoic acid ester, said ester is dispersed in an aqueous solution containing from 15% to 35% by weight of surfactant which has a kinematic viscosity of about 10 to 100 centistokes at 25% aqueous solution. Surfactants giving kinematic viscosities in the above range permit the use of sufficient quantities of said surfactants to obtain aqueous flowable concentrate compositions containing on a weight to volume basis 20% to 40% of solid, finely ground, imidazolinyl benzoic acid ester, 1.0% to 5.0% of wetting/dispersing agents, about 0.5% to 1.0% of antifoam agents, and 0.1 to 0.5% of a preservative and generally having a viscosity of from 1,000 to 3,500 centipoises as measured by a Brookfield viscometer, with a number 2 spindle at 6 rpm at 20° C. These compositions resist settling of the solid components and they do not gel. The kinematic viscosities of these surfactants measured as a 25% aqueous solution, allows the incorporation of high levels of surfactants in the final aqueous flowable compositions, without causing them to become too viscous to process and use easily. The incorporation of high levels of surfactant in the formulation provides the additional benefit that surfactants need not be incorporated during dilution of the flowable composition in a spray tank prior to application, making the compositions of this invention easier and safer to apply.

A typical stable, non-aqueous, composition of the invention comprises about 50% by weight of a isomeric mixture of solid particulate 6-(4-isopropyl-4-methyl-5-oxo-2-imidazolin-2-yl)-m-toluic acid, methyl ester and 2-(4-isopropyl-4-methyl-5-oxo-2-imidazolin-2-yl)-p-toluic acid, methyl ester and 50% by weight of sodium bisulfate.

In accordance with this invention, formulations containing an imidazolinyl benzoic acid ester as a finely divided particulate solid when dispersed in water, are herbicidally enhanced by admixture of the diluted aqueous formulation with from 1 to 3 molar equivalents of an alkali metal bisulfate, ammonium bisulfate or mixtures thereof. Such admixture generally results in adjustment of the pH of the dilute aqueous composition to a value between pH 1.0 to pH 3.8.

Among the imidazolinyl benzoic acid esters that are effectively enhanced by the method of the present invention are those represented by the structure:

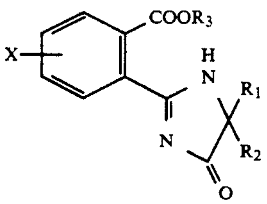

wherein X is hydrogen, alkyl $C_1$–$C_3$, halogen or nitro; $R_1$ is alkyl $C_1$–$C_4$; $R_2$ is alkyl $C_1$–$C_6$, cycloalkyl $C_3$–$C_6$, or when $R_1$ and $R_2$ are taken together with the carbon to which they are attached they may represent cycloalkyl $C_3$–$C_6$ optionally substituted with methyl; $R_3$ is alkyl $C_1$–$C_{12}$ optionally substituted with one $C_1$–$C_3$ alkoxy group or one $C_3$–$C_6$ cycloalkyl group or one phenyl group, alkenyl $C_3$–$C_5$ optionally substituted with one or two $C_1$–$C_3$ alkyl group(s) or one phenyl group or with one to two halogen substituent(s), alkynyl $C_3$–$C_5$ optionally substituted with one or two $C_1$–$C_3$ alkyl group(s) or one phenyl group or with one to two halogen substituent(s), benzyl, cyclohexenylmethyl, ethynylcyclohexyl, ethynylallyl or pentadienyl, cycloalkyl $C_3$–$C_6$ optionally substituted with one or two $C_1$–$C_3$ alkyl group(s); when $R_1$ and $R_2$ are not the same the optical isomers thereof, and the isomeric mixtures thereof.

Other imidazolinyl benzoic acid esters that are herbicidally enhanced by the method of this invention are:

2-(4-isopropyl-4-methyl-5-oxo-2-imidazolin-2-yl)benzoic acid, 2-propynyl ester;

2-(4-isopropyl-4-methyl-5-oxo-2-imidazolin-2-yl)benzoic acid, n-propyl ester;

2-(4-isopropyl-4-methyl-5-oxo-2-imidazolin-2-yl)benzoic acid, 1,1-dimethylallyl ester;

2-(4-isopropyl-4-methyl-5-oxo-2-imidazolin-2-yl)benzoic acid, allyl ester;

2-(4-isopropyl-4-methyl-5-oxo-2-imidazolin-2-yl)benzoic acid, octyl ester;

(+)-2-(4-isopropyl-4-methyl-5-oxo-2-imidazolin-2-yl)benzoic acid, ethyl ester;

(+)-2-(4-isopropyl-4-methyl-5-oxo-2-imidazolin-2-yl)benzoic acid, 2-chloroallyl ester;

(−)-2-(4-isopropyl-4-methyl-5-oxo-2-imidazolin-2-yl)benzoic acid, -2-propynyl ester; and 2-(4-isopropyl-4-methyl-5-oxo-2-imidazolin-2-yl)benzoic acid, 1-methyl-2-butenyl ester.

The present invention is further illustrated by the examples set forth below.

EXAMPLES 1–2

Preparation of Suspension concentrate Formulations Containing an Imidazolinyl Benzoic Acid Ester To a suitable vessel fitted with a propeller mixer and high shear agitation add 500 L of water. Turn on the mixer and add 7.5 kg of silicone antifoam agent, 1.5 kg of aqueous dipropylene glycol solution of 1,2-benzisothiazolin-3-one perservative and 42.9 kg of a mixture of butyl capped ethylene oxide/propylene oxide block copolymer and propylene glycol having a 1 to 3 to 1.29 ratio and 10 kg of oxythoxylated polyaryl phosphate neutralized with triethanolamine dispersing agent.

Stirring is continued to dissolve and/or disperse all the additives. Thereafter, the high-shear agitator is switched on and 250 kg of an isomeric mixture of an imidazolinyl benzoic acid ester is added. High-shear mixing is continued until a fluid, mobile slurry is achieved with retentions of less than 0.25% on 150 μ sieve. Avoid air entrainment during mixing. The thus formed slurry is then wet, milled to give a product with a particle size distribution of 90% less than 8μ and 50% less than 3μ. Thereafter the remaining water added. To this mixture 200 kg of 11 mole nonyl phenol ethoxylate is gradually introduced and stirring is continued to obtain a smooth, uniform aqueous suspension concentrate.

Compositions prepared by this method are reported in Table I below.

TABLE I

| Compound | % w/v Ex. 1 | % w/v Ex. 2 |
|---|---|---|
| 6-(4-isopropyl-4-methyl-5-oxo-2-imidazolin-2-yl)-m-Toluic acid, methyl ester and 2-(4-isopropyl-4-methyl-5-oxo-2-imidazolin-2-yl)-p-Toluic acid, methyl ester | 30.0 | 25.0 |
| Ethoxylated nonyl phenol 11 mols of ethoxylation | 15.0 | 20.0 |
| Oxyethoxylated polyaryl phosphate neutralized with Triethanolamine | 1.0 | 1.0 |
| Propylene glycol | 1.3 | 1.3 |
| Butyl capped ethylene oxide/propylene oxide block copolymer | 3.0 | 3.0 |
| Aqueous dipropylene glycol solution of 1,2-benzisothiazolin-3-one (preservative) | 0.15 | 0.15 |
| Silicone antifoam | 0.75 | 0.75 |
| Water q.s. to | 100.0 | 100.0 |

EXAMPLES 3–14

Preparation of stable aqueous flowable concentrates

The preparation of stable aqueous flowable concentrates that can be biologically enhanced by the method of the present invention when they are tank mixed in the field for dilute aqueous spray application, are generally prepared by a two step procedure as described below.

The first step involves the preparation of a ground, particulate, aqueous slurry which requires the calculation of the quantities of each ingredient required and mixing as follows: To a suitable vessel with fitted agitation, add all the water, then the antifoam agent if desired, followed by the wetting and/or dispersing agents and then the isomeric mixture of 6-(4-isopropyl-4-methyl-5-oxo-2-imidazolin-2-yl)-m-toluic acid, methyl ester and 2-(4-isopropyl-4-methyl5-oxo-2-imidazolin-2-yl-p-toluic acid, methyl ester. Gradually add this isomeric mixture with vigorous high-shear agitation until a mobile slurry results. Continue high shear-mixing until the particle size is suitable for milling, avoiding air entrainment during mixing.

Then pass the slurry through a wet-mill to give a suspension with particle size essentially 98% less than 5 microns and sample the milled slurry and analyse for active ingredient (% w/w).

The second step involves preparation of the aqueous flowable concentrate.

Calculate the weight of milled slurry required for the final product and add it to a suitable vessel fitted with efficient agitation.

Calculate the extra quantities, if any, of wetting and/or dispersing agents, the antifoam and the antifreeze required in the final product and add them to the slurry. Agitate the mixture until the mixture is homogeneous.

Calculate the quantity of extra water required and add it to the vessel and mix until homogeneous.

Gradually add and dissolve the required amount of surfactant, which as a 25% aqueous solution has a kinematic viscosity of 5 to 100 centerstokes, and mix with vigorous agitation, avoiding air entrainment.

Mix thoroughly until all the surfactant is dissolved and a smooth, uniform product is obtained.

Utilizing the above procedure yields the stable aqueous flowable compositions listed in Tables II, III and IV below.

TABLE II

Aqueous Flowable Formulations Containing an Imidazolinyl Benzoic Acid Ester

| Compound | Formulations Ex. 3 % w/v | Ex. 4 % w/v | Ex. 5 % w/v | Ex. 6 % w/v | Ex. 7 % w/v |
|---|---|---|---|---|---|
| 6-(4-isopropyl-4-methyl-5-oxo-2-imidazolin-2-yl)-m-Toluic acid, methyl ester and 2-(4-isopropyl-4-methyl-5-oxo-2-imidazolin-2-yl)-p-Toluic acid, methyl ester | 30.0 | 25.0 | 30.0 | 25.0 | 20.0 |
| Arkopal N 110 - Nonionic surfactant - Ethoxylated nonyl Phenol 11 moles EO | 12.0 | 16.0 | 15.0 | 20.0 | 20.0 |
| Soprophor FL - Dispersing Agent-oxyethoxylated polyaryl ethoxylate neutralized with triethanolamine | 4.0 | 4.0 | 4.0 | 4.0 | 4.0 |
| Silcolapse 5000 - Silicone antifoam | 0.75 | 0.75 | 0.75 | 0.75 | 0.75 |
| Proxel GXL - Preservative - aqueous dipropylene glycol solution of 1,2-benzisothiazolin-2-one | 0.15 | 0.15 | 0.15 | 0.15 | 0.15 |
| Water, to make | 100% | 100% | 100% | 100% | 100% |
| Density | 1.04 | 1.03 | 1.03 | 1.03 | 1.03 |

TABLE IV

Aqueous Flowable Concentrate Containing an Imidazolinyl Benzoic Acid Ester

| Isomeric mixture of | Ex. 10 (g/l) | Ex. 11 (g/l) | Ex. 12 (g/l) | Ex. 13 (g/l) | Ex. 14 (g/l) |
|---|---|---|---|---|---|
| 6-(4-isopropyl-4-methyl-5-oxo-2-imidazolin-2-yl)m-tolic acid, methyl ester and 2-(4-isopropyl-4-methyl-5-oxo-2-imidazolin-2-yl-toluic acid, methyl ester | 340.0 | 283.3 | 340.0 | 283.3 | 226.7 |
| Polyethoxylated nonylphenol (11 Mol EO) viscosity 15 centerstokes as a 25% aqueous solution (Nonionic surfactant) | 120.0 | 160.0 | 150.0 | 200.0 | 200.0 |
| Wetting/dispersing agent (polyethoxylated polyarylphenol phosphate, neutralized with triethanolamine) | 40.0 | 40.0 | 40.0 | 40.0 | 40.0 |
| Silicone antifoam agent | 7.5 | 7.5 | 7.5 | 7.5 | 7.5 |
| Water (Balance) | 532.5 | 539.2 | 499.2 | 499.2 | 555.8 |
| Stability: | | | | | |

| Storage time | Example No. | Average percent recovery 28° C. | 37° C. | 50° C. |
|---|---|---|---|---|
| One Month | 8-12 | 100.0 | 98.0 | 97.0 |
| Two Months | 10-12 | 99.0 | 98.0 | 98.0 |

TABLE III

Aqueous Flowable Formulations Containing an Imidazolinyl Benzoic Acid Ester

| Compound | Ex. 8 % w/v | Ex. 9 % w/v |
|---|---|---|
| 6-(4-isopropyl-4-methyl-5-oxo-2-imidazolin-2-yl)m-Toluic acid, methyl ester and 2-(4-isopropyl-4-methyl-5-oxo-2-imidazolin-2-yl)p-Toluic acid, methyl ester | 25.0 | 25.0 |
| Arkopal N 100 - Nonionic | 15.0 | 20.0 |

TABLE III-continued

Aqueous Flowable Formulations Containing an Imidazolinyl Benzoic Acid Ester

| Compound | Ex. 8 % w/v | Ex. 9 % w/v |
|---|---|---|
| surfactant - Ethoxylated nonyl Phenol 11 moles EO | | |
| Dispersing Agent - Soprophor FL/Witconol NS 500K/Propylene glycol 1/3/1.3 | 4.0 | 4.0 |
| Silicone antifoam | 0.75 | 0.75 |
| Preservative - Proxel GXL | 0.15 | 0.15 |
| Water, to make | 100.0% | 100.0% |

EXAMPLE 15

Biological enhancement of aqueous suspension concentrate formulations containing finely divided, solid, particulate imidazolinyl benzoic acid esters In these biological evaluations test samples are prepared using the 300 SC (suspension concentrate) from Example 1. The test procedure is designed to provide and evaluate the equivalent of 200, 400, 500 or 600 grams per hectare of an isomeric mixture of 6-(4-isopropyl-4-methyl-5-oxo-2-imidazolin-2-yl) -m-toluic acid, methyl ester and 2-(4-isopropyl-4-methyl-5-oxo-2-imidazolin-2-yl)-p-toluic acid, methyl ester, applied to wild oats (Avena fatua) in the 2 to 3 leaf stage. Formulations evaluated include 300 SC in water alone, 300 SC plus sodium bisulfate in water, 300 SC plus Nonionic surfactant (11 mole nonyl phenol ethoxylate) in water and 300 SC plus sodium bisulfate and nonionic surfactant (11 mole nonyl phenol ethoxylate) in water.

The test compositions are made up in water and sprayed on wild oat plants in the 2 to 3 leaf stage of development and the sprayed plants are then placed on greenhouse benches where they are cared for using normal greenhouse practices. The sprayer is designed and calibrated to deliver the equivalent of 100 liters per hectare of test solution.

Each composition is replicated four times and on days 10 and 20 after spraying, all plants are examined and the percent wild oat control determined for each treatment and recorded. The compositions evaluated and the results obtained are reported in Tables V and VI respectively.

of nonionic surfactant to the diluted suspension concentrate helps to increase the biological activity thereof. Moreover, the addition of sodium sulfate and added nonionic surfactant to the suspension concentrate containing imidazolinyl benzoic acid ester also enhances the biological activity over that obtained with the nonionic surfactant.

EXAMPLE 16

Chemical and Physical Stability of a 1:1 w/w blend of Solid Imidazolinyl Benzoic Acid Ester In this evaluation technical grade samples 98% purity of a mixture of 6-(4-isopropyl-4-methyl-5-oxo-2-imidazolin-2-yl)-m-toluic acid, methyl ester and 2-(4-isopropyl-4-methyl-5-oxo-2-imidazolin-2-yl)-p-toluic acid, methyl ester are uniformly blended on a 50/50 % w/w basis with sodium bisulfate 96% purity and then stored in glass jars at room temperature and 370° C. After four months of storage the chemical and physical characteristics of the blends show no evidence of change.

TABLE V

Suspension Concentrate Formulations for Wild Oat Control Greenhouse Test Equivalent to Spray Volume of 100 L/ha

| Treatment | | Equivalent of g/ha ai | l/ha Formulation | g/ha Sodium Bisulfate | ml/ha 50% 11 mole nonyl phenol ethoxylate |
|---|---|---|---|---|---|
| Example I | 300SC | 600 | 2.00 | — | — |
| Example I | 300SC | 500 | 1.66 | — | — |
| Example I | 300SC | 400 | 1.33 | — | — |
| Example I | 300SC | 200 | 0.67 | — | — |
| Example I | 300SC | 500 | 1.66 | — | 100 |
| Example I | 300SC | 400 | 1.33 | — | 80 |
| Example I | 300SC | 200 | 0.67 | — | 40 |
| Example I | 300SC | 500 | 1.66 | 316 | 100 |
| Example I | 300SC | 400 | 1.33 | 253 | — |
| Example I | 300SC | 200 | 0.67 | 126 | — |
| Example I | 300SC | 500 | 1.66 | 316 | 100 |
| Example I | 300SC | 400 | 1.33 | 253 | 80 |
| Example I | 300SC | 200 | 0.67 | 126 | 40 |

300SC = 30% w/v of an isomeric mixture of 6-(4-isopropyl-4-methyl-5-oxo-2-imidazolin-2-yl)m-toluic acid, methyl ester and 6-(4-isopropyl-4-methyl-5-oxo-2-imidazolin-2-yl)p-toluic acid, methyl ester

TABLE VI

% Wild Oat Control with Example I, 300SC formulation alone or in combination with sodium bisulfate, additional 11 mole nonyl phenol ethoxylate or both sodium bisulfate and additional 11 mole nonyl phenol ethoxylate

| Treatment | | | | % Oat Control 1 | 2 | 3 | 4 | Average % Control |
|---|---|---|---|---|---|---|---|---|
| Example I | 300SC | 600 | — | 75 | 85 | 80 | 85 | 81.3 |
| Example I | 300SC | 500 | — | 80 | 80 | 75 | 80 | 78.8 |
| Example I | 300SC | 400 | — | 50 | 75 | 75 | 80 | 70.0 |
| Example I | 300SC | 200 | — | 50 | 55 | 50 | 60 | 53.8 |
| Example I | 300SC | 500 | 100-(AR) | 90 | 90 | 90 | 85 | 88.8 |
| Example I | 300SC | 400 | 80-(AR) | 85 | 90 | 85 | 85 | 86.3 |
| Example I | 300SC | 200 | 40-(AR) | 80 | 80 | 75 | 80 | 78.8 |
| Example I | 300SC | 500 | 316-Sodium Bisulfate | 98 | 98 | 90 | 95 | 95.3 |
| Example I | 300SC | 400 | 253-Sodium Bisulfate | 95 | 95 | 95 | 85 | 92.5 |
| Example I | 300SC | 200 | 126-Sodium Bisulfate | 50 | 75 | 75 | 65 | 66.3 |
| Example I | 300SC | 500 | 100 + 316-AR + Sodium Bisulfate | 95 | 95 | 95 | 90 | 93.8 |
| Example I | 300SC | 400 | 80 + 253-AR + Sodium Bisulfate | 95 | 95 | 90 | 80 | 90.0 |
| Example I | 300SC | 200 | 40 + 126-AR + Sodium Bisulfate | 50 | 75 | 85 | 80 | 71.3 |

AR = 11 mole nonyl phenol ethoxylate

From the above data it can be seen that the addition of sodium bisulfate to the dilute aqueous 300SC formulations of Example 1 increases the control of wild oats from 11.5% to 22.5% over the dilute aqueous 300SC formulations alone. The data also show that the addition

EXAMPLE 17

Determination of the effect of alkali metal bisulfate on imidazolinyl benzoic acid ester solubility in different types of water using 0, 1, 2 or a molar equivalents of alkali metal bisulfate In these evaluations the 300SC concentrates of Example I, containing isomeric mixtures of 6-(4-isopropyl-4-methyl-5-oxo-2-imidazolin-2-yl)-m-toluic acid methyl ester and 2-(4-isopropyl-4-methyl-5-oxo-2-imidazolin-2-yl)-p-toluic acid, methyl ester are dispersed in water and treated with from 0 to 3 molar equivalents of sodium bisulfate based on the amount of ester used. The pH of the water was determined before admixture with the 300SC, after admixture with the 300SC and again after treatment with sodium bisulfate.

Also, each sample is assayed for the presence of the isomeric mixture of the esters and likewise for the isomeric mixture of the corresponding acids to determine where the esters are undergoing any significant hydrolysis.

The results of these evaluations are reported in Tables VII and VIII below.

TABLE VII

Determination of the effect of from 1 to 3 molar equivalents of alkali metal bisulfate on aqueous dispersions of Example I, 300SC in different type water samples

| Treatment | Water Canada A | Canada B | Canada C | NJ D |
|---|---|---|---|---|
| water pH | 8.64 | 8.64 | 8.59 | 7.40 |
| Water + 300SC pH | 8.24 milky appearance | 8.14 milky appearance | 8.14 milky appearance | 6.86 milky appearance |
| + 1 molar Equiv. $NaHSO_4$ | 5.14 No apparent change | 5.90 No apparent change | 3.82 No apparent change | 2.73 turned Hazy |
| + 2 molar Equiv. $NaHSO_4$ | 2.75 Slightly Hazy | 2.97 No apparent change | 2.61 Essentially Clear | 2.15 Essentially Clear |
| + 3 molar Equiv. $NaHSO_4$ | 2.12 Essentially Clear | 2.32 Essentially Clear | 2.10 Essentially Clear | 1.67 Essentially Clear |

TABLE VIII

Analytical determinations for the presence of Imidazolinyl Benzoic acid ester and corresponding imidazolinyl benzoic acid in filtered and unfiltered samples treated with 300SC from Example I and from 1 to 3 molar equivalents of $NaHSO_4$

| Treatments containing 300SC | % w/w Imidazolinyl Benzoic Acid Ester | % w/w Imidazolinyl Benzoic Acid |
|---|---|---|
| unfiltered Samples | | |
| A | 0.422 | 0.039 |
| B | 0.404 | 0.041 |
| C | 0.428 | 0.014 |
| D | 0.454 | 0.007 |
| filtered Samples | | |
| A | 0.187 | 0.024 |
| B | 0.183 | 0.034 |
| C | 0.194 | 0.031 |
| D | 0.214 | 0.009 |
| filtered Samples + 1 Molar Eq. $NaHSO_4$ | | |
| A | 0.204 | 0.006 |
| B | 0.206 | 0.006 |
| C | 0.240 | 0.007 |
| D | 0.457 | 0.007 |
| filtered Samples + 2 Molar Eq. $NaHSO_4$ | | |
| A | 0.436 | 0.007 |
| B | 0.365 | 0.004 |

TABLE VIII-continued

Analytical determinations for the presence of Imidazolinyl Benzoic acid ester and corresponding imidazolinyl benzoic acid in filtered and unfiltered samples treated with 300SC from Example I and from 1 to 3 molar equivalents of $NaHSO_4$

| Treatments containing 300SC | % w/w Imidazolinyl Benzoic Acid Ester | % w/w Imidazolinyl Benzoic Acid |
|---|---|---|
| C | 0.456 | 0.006 |
| D | 0.450 | 0.004 |
| filtered Samples + 3 Molar Eq. $NaHSO_4$ | | |
| A | 0.464 | 0.007 |
| B | 0.459 | 0.007 |
| C | 0.460 | 0.004 |
| D | 0.461 | 0.004 |

What is claimed is:

1. A method for enhancing the biological activity of a formulation containing a solid imidazolinyl benzoic acid ester which comprises:

(a) diluting the ester containing formulation with water; and (b) adjusting the pH of the diluted ester containing formulation to a value of about 1.0 to 3.8 by the addition of an effective amount of a bisulfate.

2. The method according to claim 1, wherein the imidazolinyl benzoic acid ester has the structure:

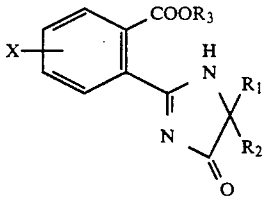

wherein X is hydrogen, an alkyl $C_1$ to $C_3$, halogen or nitro; $R_1$ is an alkyl $C_1$ to $C_4$; $R_2$ is an alkyl $C_1$ to $C_6$, a cycloalkyl $C_3$ to $C_6$, or when $R_1$ and $R_2$ are taken together with the carbon to which they are attached they may represent a cycloalkyl $C_3$ to $C_6$ optionally substituted with methyl; $R_3$ is an alkyl $C_1$ to $C_{12}$ optionally substituted with one $C_1$ to $C_3$ alkoxy group or one $C_3$ to $C_6$ cycloalkyl group or one phenyl group, an alkenyl $C_3$ to $C_5$ optionally substituted with one or two $C_1$ to $C_3$ alkyl group(s) or one phenyl group or with one to two halogen substituent(s), an alkynyl $C_3$ to $C_5$ optionally substituted with one or two $C_1$ to $C_3$ alkyl group(s) or one phenyl group or with one to two halogen substituent(s), benzyl, cyclohexenylmethyl, ethynylcyclohexyl, ethynylallyl or pentadienyl, a cycloalkyl $C_3$ to $C_6$ optionally substituted with one or two $C_1$ to $C_3$ alkyl group(s); when $R_1$ and $R_2$ are not the same the optical isomers thereof, and the isomeric mixtures thereof.

3. The method according to claim 1, wherein the imidazolinyl benzoic acid ester is an isomeric mixture of solid 6-(4-isopropyl-4-methyl-5-oxo-2-imidazolin-2-yl)-m-toluic acid, methyl ester and 2-(4-isopropyl-4-methyl-5-oxo-2-imidazolin-2-yl)-p-toluic acid, methyl ester.

4. The method according to claim 1 wherein the bisulfate is selected from the group consisting of an alkali metal bisulfate, an ammonium bisulfate or a mixture thereof.

5. The method according to claim 4 wherein the alkali metal bisulfate is selected from the group consisting of sodium bisulfate and potassium bisulfate.

6. A method for enhancing the biological activity of an herbicidal formulation containing a solid imidazolinyl benzoic acid ester which comprises:

(a) diluting the ester containing formulation; and (b) adjusting the pH of the ester containing formulation to a value of about 1.0 to 3.8 by the addition of an effective amount of an alkali metal bisulfate, an ammonium bisulfate or a mixture thereof.

7. The method according to claim 6, wherein the alkali metal bisulfate is selected from the group consisting of sodium bisulfate and potassium bisulfate.

8. A composition containing a solid imidazolinyl benzoic acid ester produced by the method in claim 6.

9. A method for increasing the biological activity of an herbicial formulation containing a solid imidazolinyl benzoic acid ester having the structure:

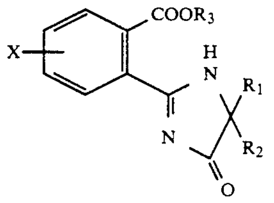

wherein X is hydrogen, an alkyl $C_1$ to $C_3$, halogen or nitro; $R_1$ is an alkyl $C_1$ to $C_4$; $R_2$ is an alkyl $C_1$ to $C_6$, a cycloalkyl $C_3$ to $C_6$, or when $R_1$ and $R_2$ are taken together with the carbon to which they are attached they may represent a cycloalkyl $C_3$ to $C_6$ optionally substituted with methyl; $R_3$ is an alkyl $C_1$ to $C_{12}$ optionally substituted with one $C_1$ to $C_3$ alkoxy group or one $C_3$ to $C_6$ cycloalkyl group or one phenyl group, an alkenyl $C_3$ to $C_5$ optionally substituted with one or two $C_1$ to $C_3$ alkyl group(s) or one phenyl group or with one to two halogen substituent(s), an alkynyl $C_3$ to $C_5$ optionally substituted with one or two $C_1$ to $C_3$ alkyl group(s) or one phenyl group or with one to two halogen substituent(s), benzyl, cyclohozonylmethyl, ethynylcyclohoxyl, ethynylallyl or pentadienyl, a cycloalkyl $C_3$ to $C_6$ optionally substituted with one or two $C_1$ to $C_3$ alkyl group(s); when $R_1$ and $R_2$are not the same the optical isomers thereof, and the isomeric mixtures thereof, by admixing with the diluted aqueous composition about 1 to 3 molar equivalents of sodium bisulfate, potassium bisulfate, ammonium bisulfate or a mixture thereof, based upon the amount of imidazolinyl benzoic acid eater in the composition.

10. The method according to claim 9 wherein the imidazolinyl benzoic acid ester is an isomeric mixture of 6-(4-isopropyl-4-methyl-5-oxo-2-imidazolin -2-yl)-m-toluic acid, methyl ester and 2-(4-isopropyl-4-methyl-5-oxo-2-imidazolin-2-yl)-p-toluic acid, methyl ester; and the bisulfate is sodium bisulfate.

11. A stable, non-aqueous, solid formulation comprising about 10% to 55% by weight of an imidazolinyl benzoic acid eater having the structure:

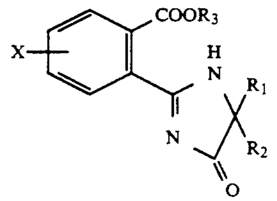

wherein X is hydrogen, an alkyl $C_1$ to $C_3$, halogen or nitro; $R_1$ is an alkyl $C_1$ to $C_4$; $R_2$ is an alkyl $C_1$ to $C_6$, a cycloalkyl $C_3$ to $C_6$, or when $R_1$ and $R_2$ are taken together with the carbon to which they are attached they may represent a cycloalkyl $C_1$ to $C_6$ optionally substituted with methyl; $R_3$ is an alkyl $C_1$ to $C_{12}$ optionally substituted with one $C_1$ to $C_3$ alkoxy group or one $C_3$ to $C_6$ cycloalkyl group or one phenyl group, an alkenyl $C_3$ to $C_5$ optionally substituted with one or two $C_1$ to $C_3$ alkyl group(s) or one phenyl group or with one to two halogen substituent(s), an alkynyl $C_3$ to $C_5$ optionally substituted with one or two $C_1$ to $C_3$ alkyl group(s) or one phenyl group or with one to two halogen substituent(s), benzyl, cyclohexenylmethyl, ethynylcyclohoxyl, ethynylallyl or pentadienyl, a cycloalkyl $C_3$ to $C_6$ optionally substituted with one or two $C_1$ to $C_3$ alkyl group(s); when $R_1$ and $R_2$are not the same the optical isomers thereof, and the isomeric mixtures thereof, and from 45% to 90% by weight of sodium bisulfate, potassium bisulfate, Ammonium bisulfate or a mixture thereof.

12. The formulation according to claim 11 consisting essentially of about 45% to 55% by weight of an isomeric mixture of 6-(4-isopropyl-4-methyl-5-oxo-2-imidazolin-2-yl)-m-toluic acid, methyl ester and 2-(4-isopropyl-4-methyl-5-oxo-2-imidazolin-2-yl)-p-toluic acid, methyl ester and about 45% to 55% by weight of sodium bisulfate.

* * * * *

UNITED STATES PATENT AND TRADEMARK OFFICE

CERTIFICATE OF CORRECTION

PATENT NO. : 5,250,502

DATED : October 5, 1993

INVENTOR(S) : Charles P. Grasso

It is certified that error appears in the above-indentified patent and that said Letters Patent is hereby corrected as shown below:

Column 14, Claim 11, line 34 should read:

--may represent a cycloalkyl $C_3$ to $C_6$ optionally substi- --"

Claim 9, Column 14, line 10 should read:

--"ester in the composition."--

Signed and Sealed this

Seventh Day of January, 1997

Attest:

BRUCE LEHMAN

*Attesting Officer*

*Commissioner of Patents and Trademarks*